United States Patent [19]

Helfer et al.

[11] 4,437,467
[45] Mar. 20, 1984

[54] APPARATUS FOR MONITORING FETAL HEARTBEAT AND THE LIKE

[75] Inventors: Joel N. Helfer, Cheshire; Phillip W. King, Wallingford, both of Conn.

[73] Assignee: American Home Products Corporation, New York, N.Y.

[21] Appl. No.: 329,799

[22] Filed: Dec. 11, 1981

[51] Int. Cl.³ .................................................. A61B 5/04
[52] U.S. Cl. ...................................................... 128/642
[58] Field of Search ................ 128/642, 639, 784–786, 128/419 P, 802

[56] References Cited

U.S. PATENT DOCUMENTS

Re. 28,990 10/1976 Hon et al. ............................ 128/642
4,180,080 12/1979 Murphy ................................ 128/642
4,281,659 8/1981 Farrar et al. ...................... 128/642 X
4,294,258 10/1981 Bernard ............................ 128/642 X
4,301,806 11/1981 Helfer .................................. 128/642
4,321,931 3/1982 Hon ..................................... 128/642

FOREIGN PATENT DOCUMENTS 2738479 3/1979 Fed. Rep. of Germany ...... 128/642

Primary Examiner—Lee S. Cohen
Attorney, Agent, or Firm—Edward M. Blocker

[57] ABSTRACT

An apparatus for use in monitoring fetal heartbeat and the like. The apparatus includes a tubular member having a distal end adapted to be inserted through the vagina and cervix of a woman in labor. A coil is movably mounted in the tubular member and is adapted to be rotatably attached to the fetus. A linear to rotary converter is provided for applying a rotary force to turn the coil for attaching to the fetus in response to the linear force applied by a user to the additional elements and additional means serve to yieldably r esist the linear force applied by the user.

6 Claims, 11 Drawing Figures

U.S. Patent  Mar. 20, 1984  Sheet 1 of 3  4,437,467
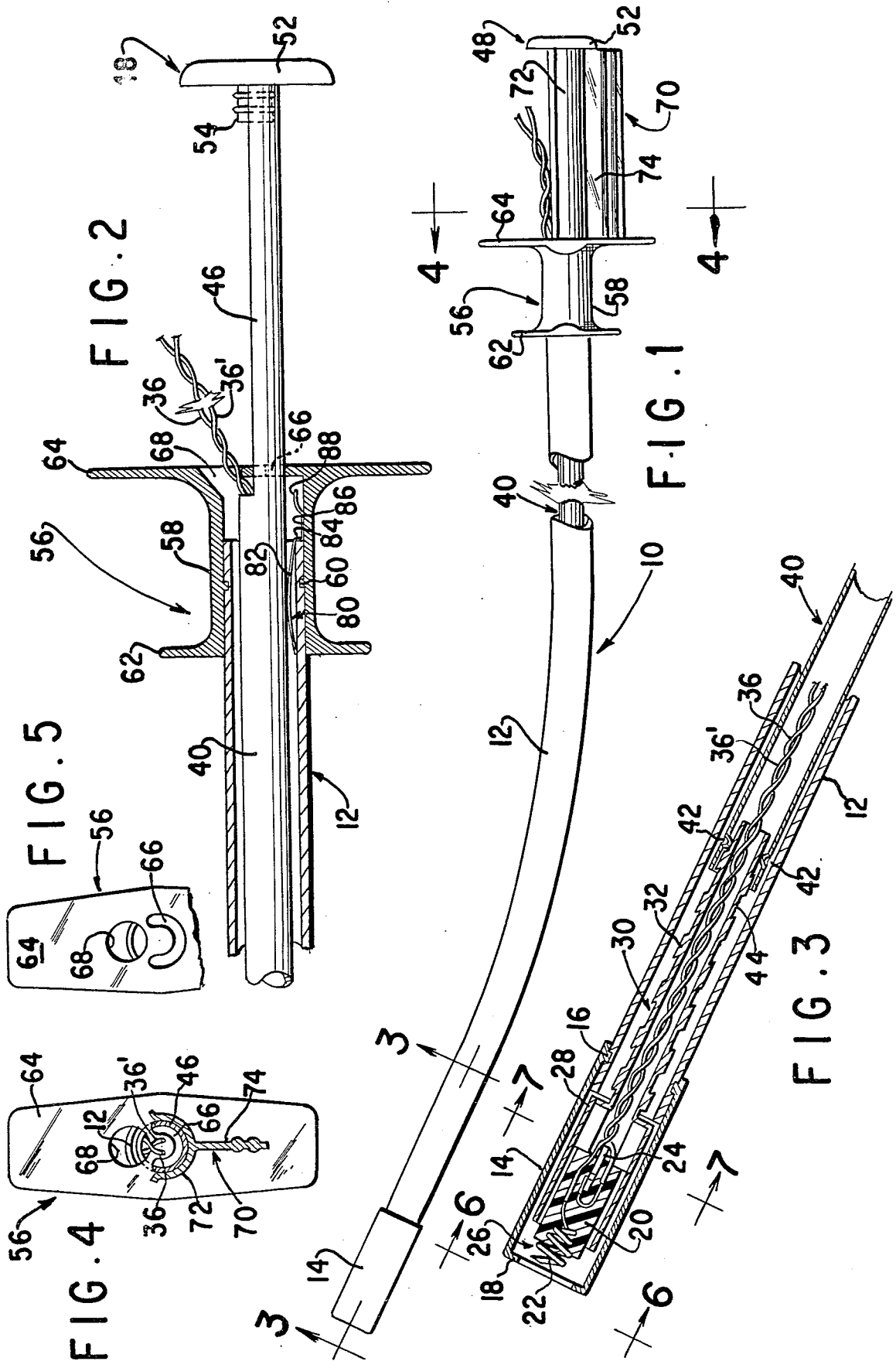

APPARATUS FOR MONITORING FETAL HEARTBEAT AND THE LIKE

BACKGROUND OF THE INVENTION

The present invention relates to fetal monitoring; more particularly, the present invention relates to improvements in fetal electrode applicators.

U.S. Reissue Pat. No. 28,990 discloses an electrode structure used in particular for detecting fetal ECG and which has found wide acceptance for direct fetal heartbeat monitoring. The electrode structure per se includes a coil electrode mounted on the distal face of a cylindrical, insulating electrode holder. A spade shaped reference electrode is mounted on the opposite, proximal face of the cyclindrical electrode holder. The electrode is disposed in the distal end of a guide tube adapted to be inserted through the vagina and cervix of a woman in labor. A drive tube is disposed within the guide tube and has a distal end provided with a notch to receive the reference electrode of the electrode structure. The drive tube extends through the guide tube to a proximal end which extends outwardly of the proximal end of the guide tube so that it may be grasped by a physician. Once the physician has introduced the distal end of the guide tube through the vagina and cervix to the fetal scalp, the physician rotates the drive tube to impart a rotational motion to the electrode structure thus to cause the coil electrode to affix to the fetal scalp.

With this prior art arrangement, the physician is enabled easily to sense the point at which the coil electrode has become fully embedded in the fetal scalp. This is important in that excessive rotation of the electrode holder may cause a laceration of the fetal scalp, while insufficient rotation of the coil electrode may result in its coming loose from the fetal scalp resulting in a loss of the hearbeat signal and possible injury to maternal tissues.

In order to render such a device easier to use, it is desirable to eliminate the need for the drive tube to be rotated manually. In U.S. patent application Ser. No. 21,550 filed Mar. 20, 1979 in the name of Edward D. Hon, a plunger is mounted within the guide tube and, when moved toward the distal end of the guide tube by a force applied thereto by the physician, causes a helical thread-type means to rotate the holder and the spiral retaining coil into the fetal epidermis. However, the use of this arrangement tends to reduce the physician's ability to sense when the coil electrode has been fully embedded in the fetal scalp, or whether it has penetrated the scalp at all.

SUMMARY

In accordance with one aspect of the present invention, an apparatus is provided for use in monitoring fetal heartbeat and the like. The apparatus comprises a tubular member having a distal end adapted to be inserted through the vagina and cervix of a woman in labor. A coil is movably mounted in the tubular member, the coil being adapted to be rotatably attached to the skin of the fetus. Means are provided for applying a rotary force to turn the coil for attaching to the fetus in response to a linear force applied by a user to the applying means. The apparatus further comprises means for enabling the user to sense resistance to the turning of the coil whereby the user may detect that the coil has penetrated the fetal skin. The user is thus able to tell whether the electrode is attached to the fetus, so as to avoid injury to maternal tissues caused by a loose electrode and ensure that the fetal ECG is detected reliably.

In accordance with a preferred embodiment of the present invention, the enabling means comprises means for yieldably resisting the linear force applied by the user. By thus requiring the user to apply force to overcome the yieldably resisting means in order to turn the coil, the user's sensitivity to an incremental increase in the reactive force which the user experiences tends to be heightened. Accordingly, the ability to sense that the coil has become embedded in the fetal scalp which is manifest as a slight increase in the reactive force is improved.

BRIEF DESCRIPTION OF THE DRAWINGS

The present invention, as well as further objects and features thereof, will be understood more clearly and fully from the following description of certain preferred embodiments, when read with reference to the accompanying drawings, in which:

FIG. 1 is a plan view of an apparatus in accordance with the present invention, shown partially broken away;

FIG. 2 is a partially sectional view of the proximal end of the apparatus of FIG. 1;

FIG. 3 is a partially sectional view of the distal end of the apparatus of FIG. 1;

FIG. 4 is a sectional view taken along the lines 4—4 in FIG. 1;

FIG. 5 is a plan view of the proximal end of a finger grip for use in the apparatus of FIG. 1, shown partially broken away;

DETAILED DESCRIPTION OF PREFERRED EMBODIMENTS

Figure 6:
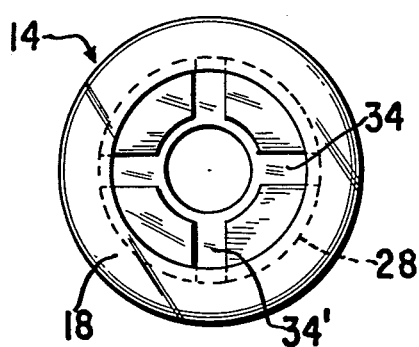
FIG. 6 is a plan view of the distal end of the apparatus of FIG. 1, taken along the lines 6—6 of FIG. 3.

With reference to FIG. 1, a fetal electrode applicator apparatus 10 includes a guide tube 12 which is form-sustaining and curved to facilitate insertion of the tube through the vagina and cervix of a woman in labor. The guide tube 12 may be made, for example, of nylon. Attached to a distal end of the guide tube 12 is an end cap 14. With reference also to FIG. 3, the end cap 14 is generally tubular and has an inwardly facing annular flange 16 which mates with an annular groove in the distal end of the guide tube 12 to retain the end cap 14 thereon. The end cap 14 is also provided with an inwardly facing annular lip 18 at its distal end. Lip 18 defines a distal opening in the end cap 14. End cap 14 may be made, for example, of polypropylene.

A generally cylindrical electrode holder 20 is slidably and rotatably disposed within the end cap 14. Electrode holder 20 may be made, for example, of an insulating plastic. A metallic coil electrode 22 is embedded in and projects from a distal end of the electrode holder 20. A spade shaped, metallic reference electrode 24 is embedded in the electrode holder 20 and projects from a proximal end thereof. The electrode holder 20, together with the coil electrode 22 and the reference electrode 24 comprise an electrode assembly indicated generally by 26.

Figure 7:
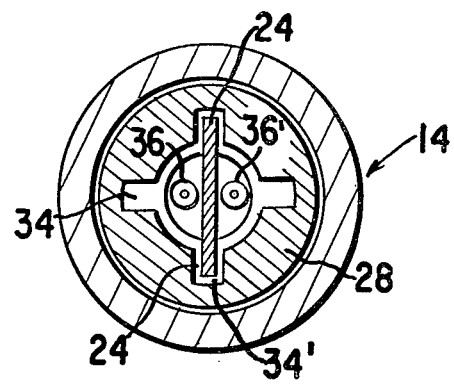
FIG. 7 is a sectional view taken along the lines 7—7 in FIG. 3.
Figure 8:
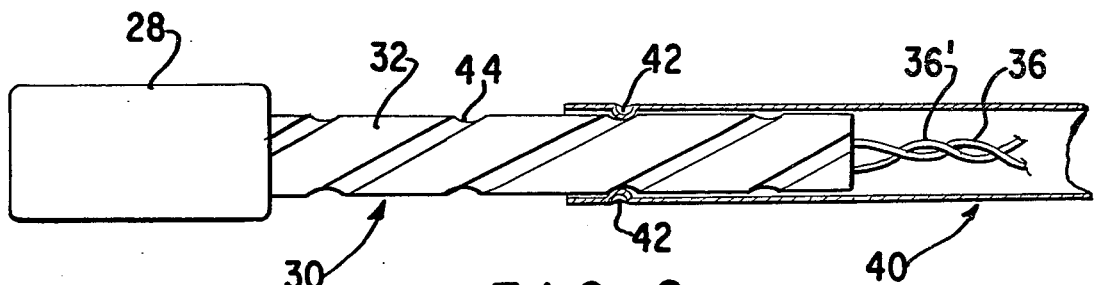
FIG. 8 is a partially sectional view of the distal end of an applying means for use in the apparatus of FIG. 1.

With reference to FIGS. 3 and 8, the electrode assembly 26 is carried in a seat 28 of a linear to rotary force converter 30. Converter 30 also includes a drive stem 32 integral with the seat 28 and projecting therefrom towards the proximal end of the guide tube 12. With reference to FIG. 6, the seat 28 (from which electrode assembly 26 has been removed) has two axially extending slots 34 and 34' each of which may serve to receive the reference electrode 24, such that when the converter 30 is rotated, it imparts a rotational force to the electrode assembly 26. As shown in FIG. 7, the reference electrode 24 is held in slot 34'. Extending through both the seat 28 and the drive stem 32, is a hollow central area which permits a pair of twisted wires 36 and 36' to extend from the electrode holder 20 therethrough toward the proximal end of the guide tube 12. Each of the wires 36 and 36' serves to connect one of coil electrode 22 and reference electrode 24 to an input terminal of a fetal monitoring device after the electrode assembly 26 has been applied to a fetal scalp, as described hereinbelow.

The converter 30 cooperates with a drive tube 40 to advance the coil electrode outwardly of the lips 18 of end cap 14 and thereafter to apply a rotary force to the electrode assembly 26 to turn the coil electrode 22 for attaching to the fetus. In this regard, a linear motion of the drive tube 40 toward the distal end of the guide tube 12 imparts a linear force to the drive stem 32 through a pair of inwardly facing dimples 42 of drive tube 40 which engage a helical groove 44 in the outer surface of drive stem 32. Upon the initial application of the linear force moving the drive tube 40 toward the distal end of the guide tube 12, the converter 30 is forced axially from the distal end of the guide tube thus to carry the electrode assembly 26 outwardly of the lip 18 of end cap 14 to permit the coil electrode 22 to contact the fetal scalp. At this point the seat 28 of converter 30 is prevented from further axial motion by the inwardly facing lip 18. Consequently, further linear motion of the drive tube 40 causes the converter 30 to rotate as the dimples 42 travel through the helical groove 44 in drive stem 32. The rotary motion of the converter 30 applies a rotary force to the electrode assembly 26 through the reference electrode 24 thus to cause the coil electrode 22 to pierce the fetal scalp and attach therein. The converter 30 may be made, for example, of acetal, while the drive tube 40 may be made, for example, of polyvinylchloride.

With reference to FIGS. 1 and 2, it will be seen that the drive tube 40 extends through guide tube 12 and outwardly of a proximal end thereof. Drive tube 40 has a proximal portion 46 from which a radial section has been removed such that proximal portion 46 has a semi-cylindrical cross section (refer to FIG. 4). A finger press 48 is affixed to the proximal end of drive tube 40. Finger press 48 has a generally flat circular portion 52 against which the doctor applies finger pressure when applying the electrode assembly 26 to the fetus, as described below, and a stem 54 by which the finger press 48 is affixed to the proximal portion 46 of drive tube 40. Finger press 48 may be made, for example, of polyvinyl chloride and may be affixed to drive tube 40 by ultrasonic bonding.

With reference to FIGS. 1, 2, 4 and 5, the electrode applicator apparatus 10 further comprises a finger hold 56 affixed to the proximal end of the guide tube 12. Finger hold 56 may be made, for example, of polypropylene. With reference especially to FIG. 2, the finger hold 56 includes a central cylindrical portion 58 which fits over the proximal end of guide tube 12 and is affixed thereto by means of an inwardly facing annular lip 60 which fits in a corresponding annular groove in the guide tube 12. Finger hold 56 also includes a distal flange 62 projecting radially from the distal end of cylindrical portion 58 and a proximal flange 64 projecting radially from the proximal end of cylindrical portion 58. Finger hold 56 provides a means whereby the physician may grasp the proximal end of the electrode applicator apparatus 10 in the same manner in which he would grasp a syringe to give an injection to a patient. With reference especially to FIG. 5, the proximal flange 64 has a crescent shaped aperture therein, indicated at 66, to permit the drive tube 46 to move therethrough axially of the guide tube 12.

Proximal flange 64 also has a circular aperture indicated at 68, through which the twisted wires 36 and 36' pass outwardly at their proximal end (refer also to FIG. 2). Circular aperture 68 is positioned eccentrically of the drive tube 46, such that when the drive tube is fully retracted toward the proximal end of the apparatus 10, the wires 36 and 36' are wedged between the drive tube 40 at the distal end of portion 46 and the proximal flange 64 of finger hold 56. Accordingly, so long as the drive tube is fully retracted toward the proximal end of the apparatus 10, the wires 36 and 36' will be prevented from moving axially through drive tube 40. By pulling wires 36 and 36' taut at the proximal end thereof when retracting the drive tube 40 fully toward the proximal direction, the electrode assembly 26 is held within the seat 28 of converter 30 unless the drive tube 40 is caused to move distally.

In order to prevent this occurrence prior to such time as it is desired to apply the electrode assembly 26 to the fetal scalp, a removable locking device 70 is provided. Refer to FIGS. 1 and 4. Locking device 70 has a semi-cylindrical portion 72 adapted to fit over proximal portion 46 of drive tube 40 and to space the circular portion 52 of finger press 48 from the proximal flange 64 of finger hold 56. The axial dimension of portion 72 is selected such that the drive tube 40 must be fully retracted proximally to permit portion 72 to fit between finger press 48 and finger hold 56, thus to insure that the wires 36 and 36' remain wedged between drive tube 40 and proximal flange 64 and to maintain the electrode assembly 26 fully retracted within end cap 14. Locking device 70 is also provided with a flange 74 integral with and projecting from portion 72, thus to permit the locking device 70 to be removed from the apparatus 10 when it is desired to apply the electrode assembly 26 to the fetal scalp. Locking device 70 may be made, for example, of polyethylene.

Figure 9:
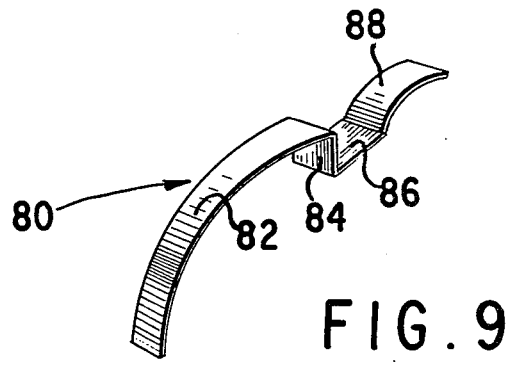
FIG. 9 is a perspective view of a leaf spring for use in the apparatus of FIG. 1.

As noted hereinabove, the drive tube 40 and the converter 30 provide a means for applying a rotary force to turn the electrode assembly 26 to cause the coil electrode 22 likewise to turn for attaching it to the fetus in response to a linear force applied by a user to the drive tube 40 through the finger press 48. The drive tube 40 together with the finger press 48 thus acts as a plunger to transmit a linear force from the doctor's finger to the converter 30 which thus serves to convert this linear force to a rotary force for rotating the electrode assembly 26. With reference to FIGS. 2 and 9, a leaf spring 80 made, for example, of stainless steel, is compressed between the plunger 40 on the one hand and the guide tube 12 and the cylindrical portion 58 of the finger hold 56, on the other hand. The leaf spring 80 includes a first, relatively long arcuate portion 82 which contacts the inside surface of the guide tube 12 at a distal end of leaf spring 80 and has a convex surface which presses against the drive tube 40. The first arcuate portion 82 of leaf spring 80 joins a linear segment 84 of leaf spring 80 at a first edge of segment 84. A second edge of segment 84 joins the first edge of a flat base segment 86 of leaf spring 84 at a 90 degree angle thereto. Segment 86 rests against the inside surface of cylindrical portion 58 of finger hold 56. A second edge of base segment 86 is joined with a short second arcuate portion 88 of leaf spring 80.

Since leaf spring 80 is compressed between drive tube 40, guide tube 12 and finger hold 56, any axial motion of drive tube 40 is yieldably resisted by the frictional force exerted thereagainst by leaf spring 80. Accordingly, the amount of force that the doctor must apply to the finger press 48 is increased which tends to improve his sensitivity to the reactive force as experienced by the coil electrode 22 as it penetrates the fetal scalp and rotates into it. Accordingly, since the doctor is thus enabled to sense resistance to the turning of the coil, his ability to both sense when the coil electrode has penetrated the fetal scalp and detect when the coil electrode has become fully embedded therein is improved. Consequently, the doctor's task is made relatively easier and the likelihood of injury to the fetus and the mother is reduced. In addition, should the locking device 70 become separated from the drive tube prematurely, the leaf spring 80 will resist distal extension of the drive tube 40 which would cause the electrode assembly 26 to be loosened undesirably.

It will be appreciated that in place of leaf spring 80, other types of devices could be used. In an alternative embodiment, a small piece of rubber is compressed between the inside surface of the cylindrical portion 58 and the drive tube 40. Moreover, such a device could be utilized to introduce a yieldably resisting force between the converter 30 and the guide tube 12. As a further alternative, a coil spring is positioned between finger press 48 and finger hold 56 such that depression of finger press 48 compresses the coil spring whereby it resists the depression of the finger press 48.

Figure 10:
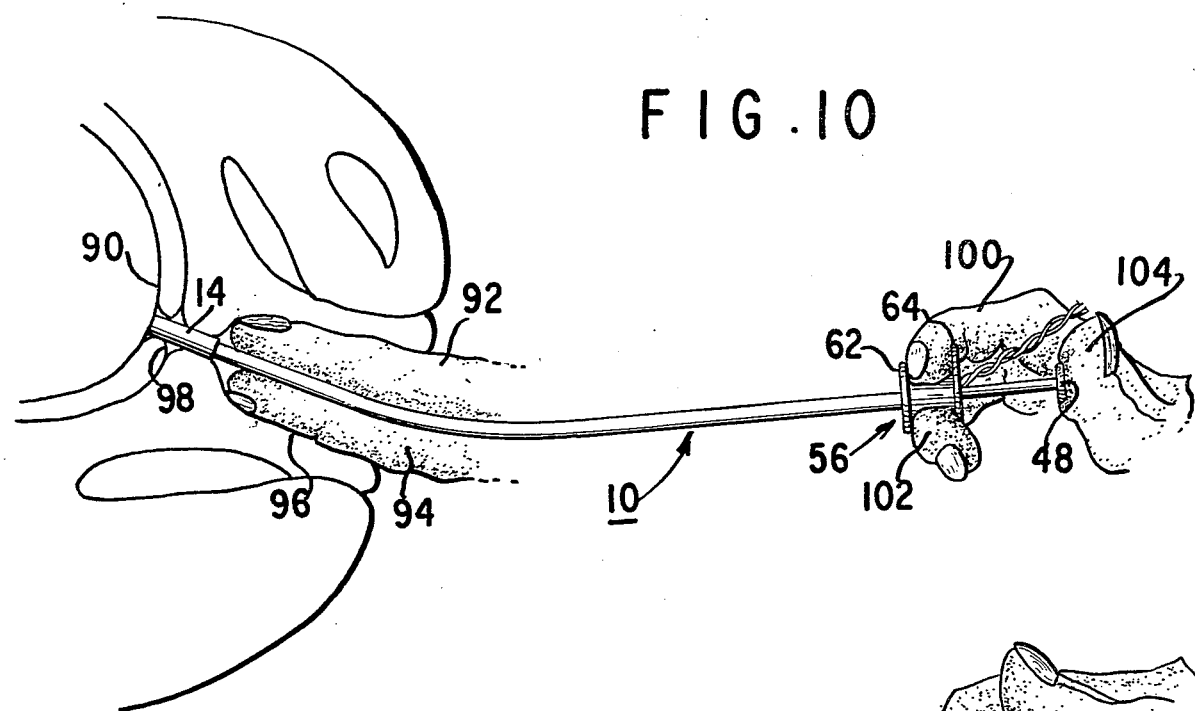
FIG. 10 is a diagrammatic view illustrating one aspect of a method for applying a coil electrode to a fetal scalp during labor using the apparatus of FIGS. 1-9.
Figure 11:
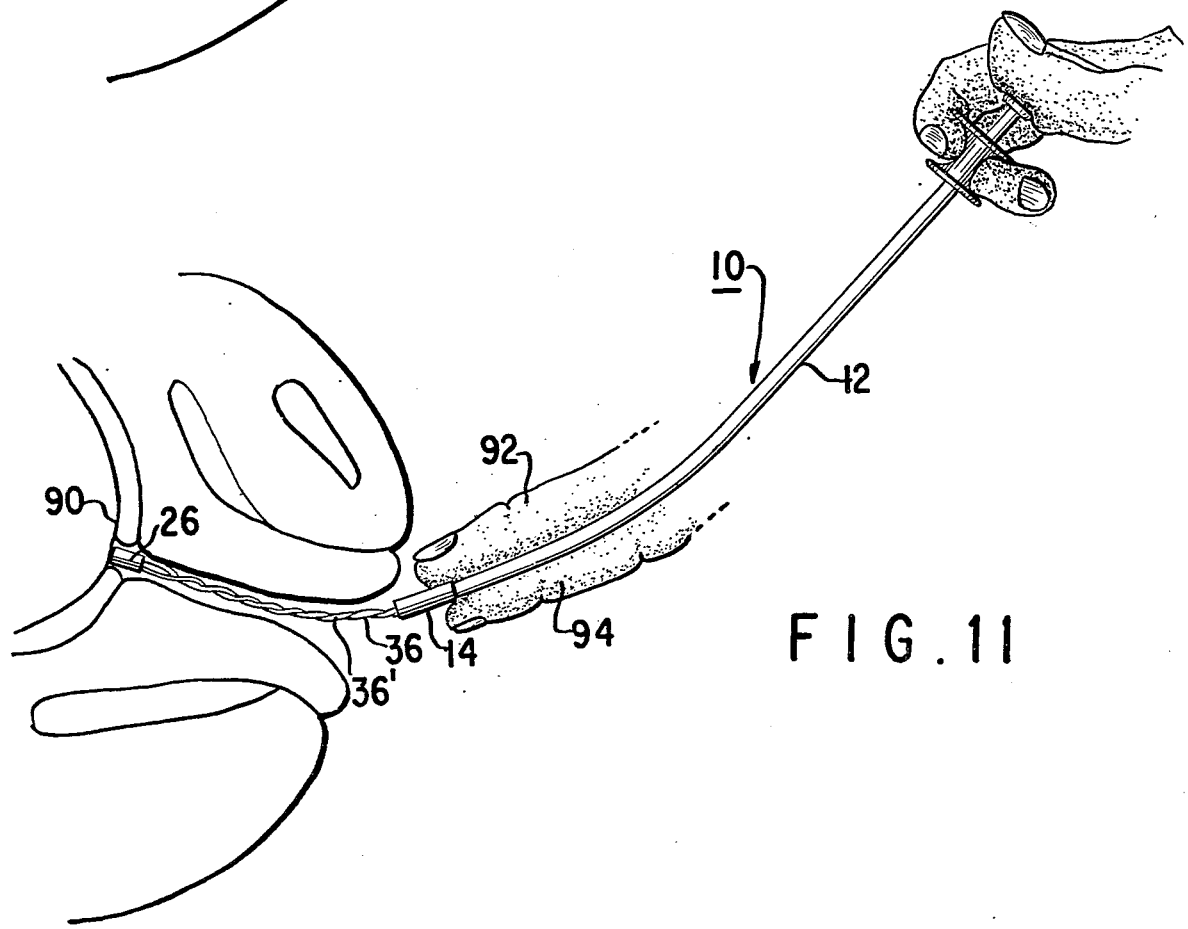
FIG. 11 is a further aspect of the method illustrated in FIG. 10.

FIGS. 10 and 11 illustrate a method whereby the electrode assembly is applied to the fetal presenting part. After the doctor has clearly identified the fetal presenting part 90, he checks to insure that the electrode assembly 26 is retracted within the end cap 14. With reference to FIG. 10, the doctor then places the distal end of the guide tube between his examining fingers 92 and 94 and advances the distal end of the apparatus through the vagina 96 and cervix 98 until the distal end of end cap 14 reaches the presenting part 90. At this point he removes the locking device 70 by grasping its flange 74 nearest the proximal flange 64 of finger hold 56 and pulling it from the drive tube 40. The doctor then places the index and middle fingers, 100 and 102, of his free hand between the flanges 62 and 64 of finger hold 56 and with forward pressure against the distal flange 62, he presses the finger press 48 in the distal direction with his thumb 104 to advance the electrode assembly 26 from the end cap 14 and rotate it to cause the coil electrode 22 to penetrate and affix to the fetal presenting part 90. With reference to FIG. 11, the doctor then slides the applicator apparatus 10 off the electrode wires 36 and 36' while removing the apparatus 10 from the vagina 96. Thereupon the wires 36 and 36' may be attached to the terminals of a fetal monitoring device for monitoring the fetal ECG.

The terms and expressions which have been employed are used as terms of description and not of limitation, and there is no intention in the use of such terms and expressions of excluding any equivalents of the features shown and described, or portions thereof, it being recognized that various modifications are possible within the scope of the invention claimed.

What is claimed is:

1. An apparatus for use in monitoring fetal heartbeat and the like, comprising:
   a tubular member having a distal end adapted to be inserted through the vagina and cervix of a women in labor;
   an electrode assembly movably mounted in the tubular member, the assembly having a coil being adapted to be rotatably introduced into the skin of a fetus for attachment thereto to permit the electrode assembly to detect a biosignal from a fetus;
   means for transmitting a signal detected by the electrode assembly;
   means for applying a rotary force to turn the coil in response to a linear force applied by a user to the applying means for introducing the coil into the fetal skin; and
   means for yieldably resisting the linear force applied by the user for enabling the user to sense resistance to the turning of the coil whereby the user may detect that the coil has penetrated the fetal skin.

2. The apparatus of claim 1, wherein the applying means is movably disposed within the tubular member and the resisting means comprises means for producing a frictional force between the tubular member and the applying means tending to resist motion of the applying means with respect to the tubular member upon application of the force by the user.

3. The apparatus of claim 2, wherein the applying means comprises converter means for converting a linear force applied thereto to a rotary force for rotating the coil, and plunger means adapted to receive the linear force applied by the user, for transmitting the linear force to the converter means for rotating the coil, and wherein the means for producing a frictional force comprises resilient means compressed between the plunger means and the tubular member.

4. The apparatus of claim 3, wherein the resilient means comprises a leaf spring.

5. The apparatus of claim 2, wherein the resisting means comprises resilient means compressed between the applying means and the tubular member.

6. The apparatus of claim 5, wherein the resilient means comprises a leaf spring.

* * * * *